US011925745B1

United States Patent
Boyle, Jr. et al.

(10) Patent No.: US 11,925,745 B1
(45) Date of Patent: Mar. 12, 2024

(54) CLEARANCE SYSTEM FOR MEDICAL TUBES SUCH AS SURGICAL DRAINS

(71) Applicant: ClearFlow, Inc., Irvine, CA (US)

(72) Inventors: Edward M. Boyle, Jr., Bend, OR (US); Wayne A. Noda, Mission Viejo, CA (US)

(73) Assignee: CLEARFLOW, INC., Irvine, CA (US)

( * ) Notice: Subject to any disclaimer, the term of this patent is extended or adjusted under 35 U.S.C. 154(b) by 246 days.

(21) Appl. No.: 17/104,515

(22) Filed: Nov. 25, 2020

Related U.S. Application Data

(60) Provisional application No. 62/941,252, filed on Nov. 27, 2019.

(51) Int. Cl.
*A61M 1/00* (2006.01)

(52) U.S. Cl.
CPC .............. *A61M 1/83* (2021.05); *A61M 1/84* (2021.05); *A61M 2209/10* (2013.01)

(58) Field of Classification Search
CPC ...... A61M 1/83; A61M 1/84; A61M 2209/10; A61M 2025/0019; A61M 16/0427; B08B 9/043; B08B 1/008; B08B 9/0535; B08B 9/04; B08B 9/027; E03C 1/30; E03C 1/302
See application file for complete search history.

(56) References Cited

U.S. PATENT DOCUMENTS

| | | | | |
|---|---|---|---|---|
| 958,854 A | * | 5/1910 | Bunn | A61B 17/3417 452/69 |
| 2,261,687 A | * | 11/1941 | Lowry | E03F 9/002 15/104.31 |
| 3,626,950 A | * | 12/1971 | Schulte | A61M 1/84 604/268 |
| 5,000,260 A | * | 3/1991 | Fontenot | B08B 9/0436 166/173 |
| 5,003,657 A | * | 4/1991 | Boiteau | B08B 9/0436 15/104.18 |
| 5,297,310 A | * | 3/1994 | Cox | B08B 9/0436 15/106 |
| 5,465,448 A | * | 11/1995 | Tajima | B08B 9/0436 15/104.07 |
| 5,628,733 A | * | 5/1997 | Zinreich | A61M 27/00 604/267 |
| 5,643,198 A | * | 7/1997 | Cucin | A61M 1/84 604/902 |
| 5,987,683 A | * | 11/1999 | Leiman | F41A 31/02 15/104.19 |

(Continued)

FOREIGN PATENT DOCUMENTS

| | | | | |
|---|---|---|---|---|
| WO | WO-2004098654 A2 | * | 11/2004 | ............. A61B 90/70 |
| WO | WO-2006071855 A2 | * | 7/2006 | ....... A61B 17/22031 |

*Primary Examiner* — Erich G Herbermann
*Assistant Examiner* — Peter Daniel Smith
(74) *Attorney, Agent, or Firm* — Pearne & Gordon LLP

(57) ABSTRACT

A device for clearing obstructions from a medical tube includes an elongated guide member residing at least partially with the medical tube. In a resting state, clearance members positioned along the guide member are in a low-profile configuration and allow a substantially unobstructed flow through a lumen of the medical tube. In use, the clearance members are in an enlarged-profile configuration to break up and clear obstructions from within the lumen of the medical tube.

12 Claims, 13 Drawing Sheets

(56) References Cited

U.S. PATENT DOCUMENTS

| | | | |
|---|---|---|---|
| 6,168,579 B1* | 1/2001 | Tsugita | A61B 17/12136 604/509 |
| 6,276,018 B1* | 8/2001 | Leiman | F41A 29/02 15/104.095 |
| 6,318,368 B1* | 11/2001 | Morejon | A61M 1/83 128/202.28 |
| 6,725,492 B2* | 4/2004 | Moore | B08B 9/0436 15/104.16 |
| 6,866,657 B2* | 3/2005 | Shchervinsky | A61M 27/00 604/266 |
| 7,051,737 B2* | 5/2006 | Kolobow | A61M 16/0488 128/207.14 |
| 7,854,728 B2* | 12/2010 | Boyle, Jr. | A61M 16/0463 15/104.16 |
| 7,951,243 B2* | 5/2011 | Boyle, Jr. | B08B 9/0436 134/8 |
| 8,157,919 B2* | 4/2012 | Vazales | A61B 90/70 134/8 |
| 8,246,752 B2* | 8/2012 | Boyle, Jr. | A61B 90/70 134/8 |
| 8,382,908 B2* | 2/2013 | Vazales | A61B 1/126 134/8 |
| 8,490,235 B2* | 7/2013 | Soetermans | B08B 9/0436 15/104.16 |
| 8,734,374 B2* | 5/2014 | Aklog | A61M 1/79 604/6.11 |
| 9,131,988 B2* | 9/2015 | Bagwell | A61M 16/0463 |
| 9,358,591 B2* | 6/2016 | Cruz | A61M 16/0875 |
| 9,638,486 B2* | 5/2017 | Evans | F41A 29/02 |
| 9,743,943 B2* | 8/2017 | Honda | A61B 17/22 |
| 9,987,027 B2* | 6/2018 | Ben-Ami | A61B 17/22031 |
| 10,047,508 B2* | 8/2018 | Elliott | E03C 1/302 |
| 10,342,902 B2* | 7/2019 | Bagwell | A61M 39/22 |
| 10,357,601 B1* | 7/2019 | Flora | A61M 25/0074 |
| 10,456,555 B2* | 10/2019 | Garrison | A61M 25/0108 |
| 10,478,125 B2* | 11/2019 | Freitag | A61M 25/0082 |
| 10,500,360 B1* | 12/2019 | Zachar | A61M 16/0463 |
| 10,537,695 B1* | 1/2020 | Salinas | B08B 9/0436 |
| 10,792,056 B2* | 10/2020 | Vale | A61B 17/221 |
| 10,881,484 B2* | 1/2021 | Boyle, Jr. | A61M 27/00 |
| 10,926,303 B1* | 2/2021 | Salinas | B08B 9/027 |
| 10,932,797 B2* | 3/2021 | Thomas | A61B 17/22 |
| 10,974,023 B2* | 4/2021 | O'Keefe | A61M 25/0026 |
| 11,255,160 B2* | 2/2022 | Al-Qasim | E21B 37/02 |
| 2003/0209258 A1* | 11/2003 | Morejon | A61M 1/83 134/166 C |
| 2004/0181194 A1* | 9/2004 | Perkins | B08B 9/0436 134/8 |
| 2005/0154373 A1* | 7/2005 | Deutsch | A61M 25/0045 604/540 |
| 2005/0267421 A1* | 12/2005 | Wing | A61B 90/70 604/267 |
| 2006/0200169 A1* | 9/2006 | Sniffin | A61B 17/00234 606/113 |
| 2006/0200183 A1* | 9/2006 | Gardocki | A61M 1/84 606/190 |
| 2006/0264988 A1* | 11/2006 | Boyle | A61B 90/70 606/159 |
| 2006/0276814 A1* | 12/2006 | Omata | A61B 17/22 606/159 |
| 2006/0287667 A1* | 12/2006 | Abela | A61B 17/320758 606/200 |
| 2008/0171985 A1* | 7/2008 | Karakoca | A61M 25/10 604/164.01 |
| 2011/0022075 A1* | 1/2011 | Christiansen | A61M 25/0023 604/524 |
| 2011/0040286 A1* | 2/2011 | Boyle, Jr. | A61M 1/83 604/540 |
| 2011/0186052 A1* | 8/2011 | Morejon | A61M 16/0434 128/207.14 |
| 2013/0304082 A1* | 11/2013 | Aklog | A61B 17/22 606/127 |
| 2014/0090194 A1* | 4/2014 | Stadelman | A61M 16/0463 15/104.05 |
| 2014/0090195 A1* | 4/2014 | Stadelman | A61M 16/04 15/104.05 |
| 2014/0276633 A1* | 9/2014 | Visveshwara | A61J 15/0003 604/524 |
| 2015/0150640 A1* | 6/2015 | Boyle | A61M 25/00 604/543 |
| 2015/0231313 A1 | 8/2015 | Okeefe et al. | |
| 2015/0231361 A1* | 8/2015 | O'Keefe | A61M 25/0026 604/164.13 |
| 2015/0367106 A1* | 12/2015 | Nitsan | A61B 1/122 604/528 |
| 2016/0001036 A1* | 1/2016 | Nickerson | A61M 25/00 604/540 |
| 2018/0230689 A1* | 8/2018 | Schaafsma | B08B 9/043 |
| 2019/0076619 A1* | 3/2019 | Boyle | A61B 90/70 |
| 2019/0217055 A1* | 7/2019 | Johnston | A61M 25/0017 |
| 2019/0321525 A1* | 10/2019 | Aklog | A61M 1/76 |
| 2020/0022777 A1* | 1/2020 | Rama | A61M 25/00 |
| 2020/0038627 A1* | 2/2020 | Elsasser | A61M 25/00 |
| 2021/0121667 A1* | 4/2021 | Howell | A61M 25/09041 |
| 2021/0170127 A1* | 6/2021 | Salinas | B08B 9/0436 |
| 2021/0196924 A1* | 7/2021 | O'Keefe | A61M 1/84 |
| 2021/0290914 A1* | 9/2021 | Burkholz | A61M 25/0097 |

\* cited by examiner

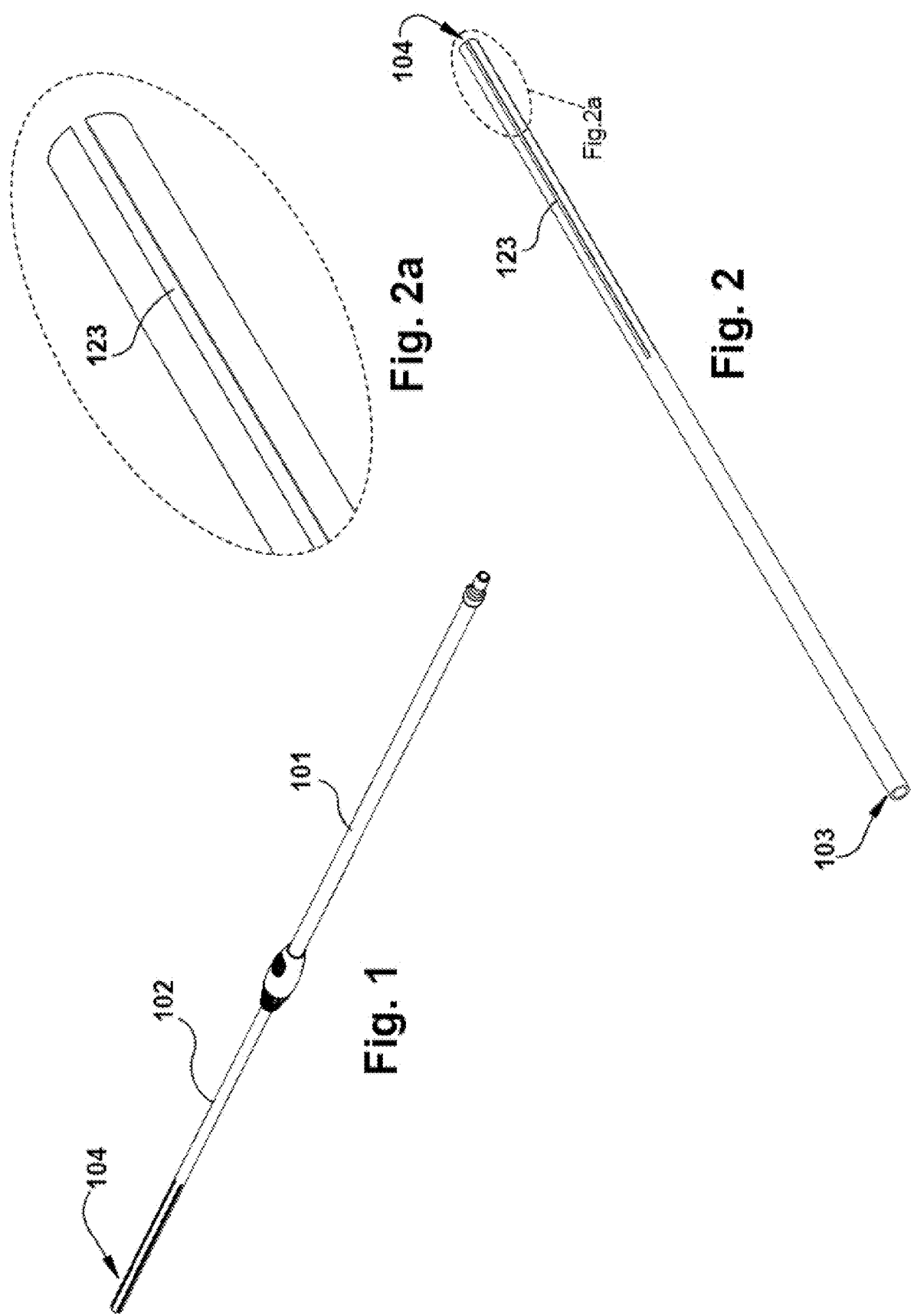

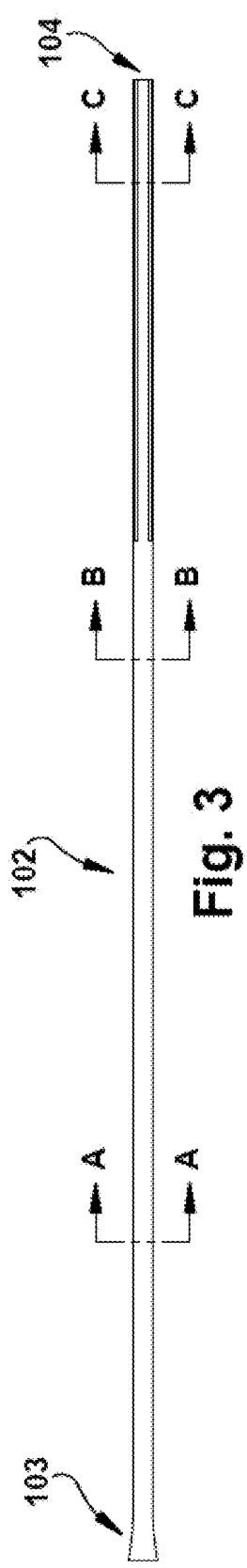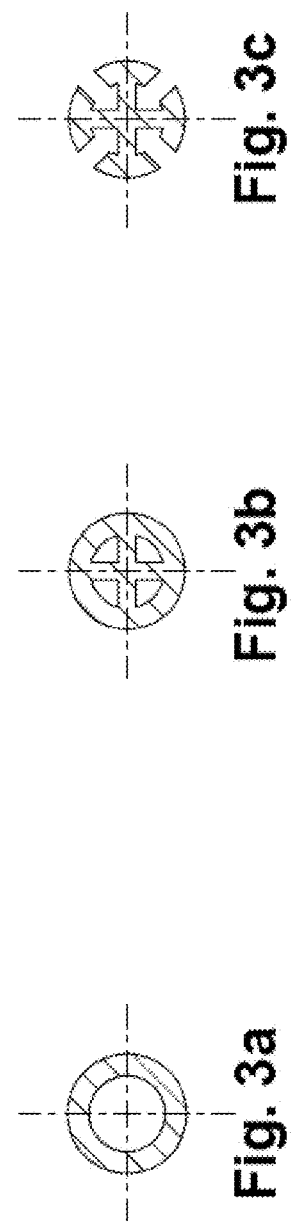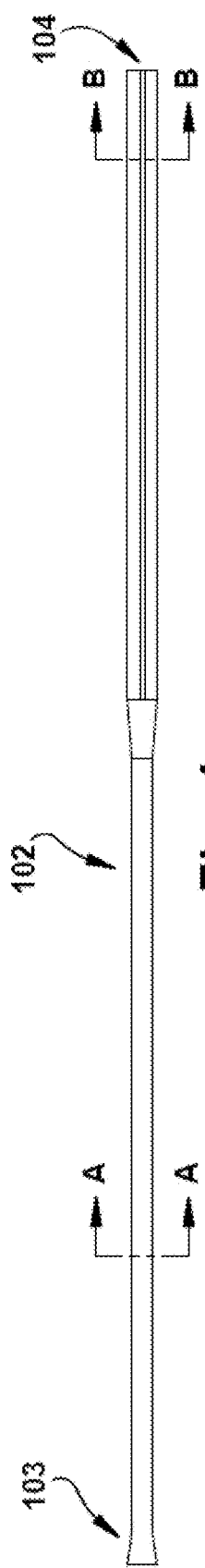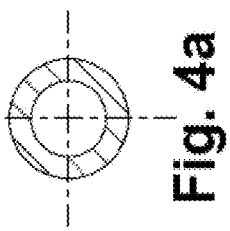

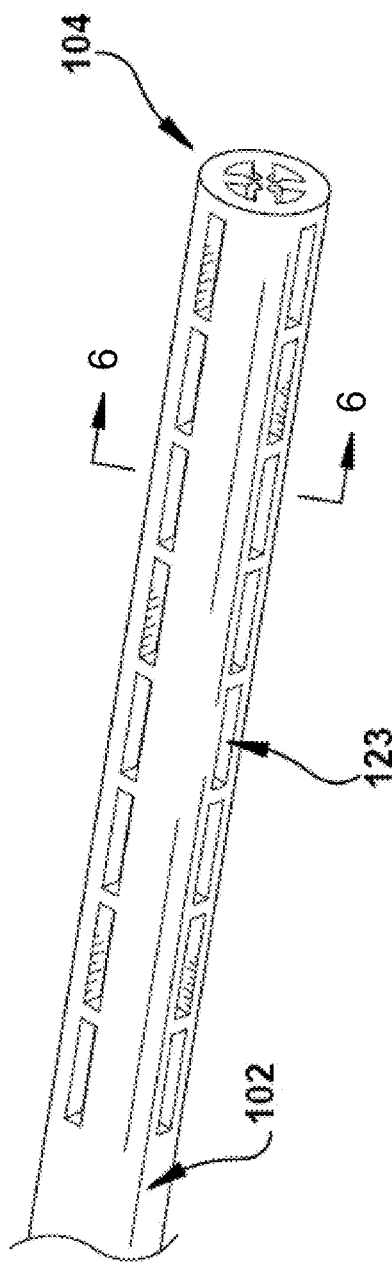
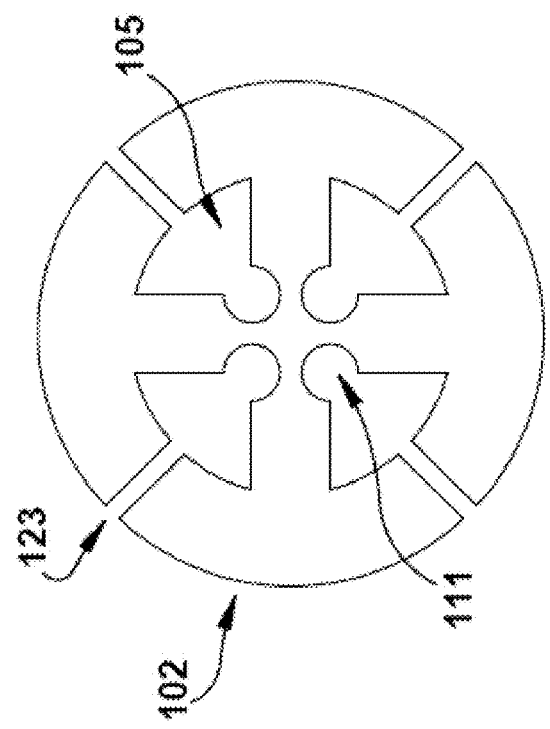
Fig. 5
Fig. 6

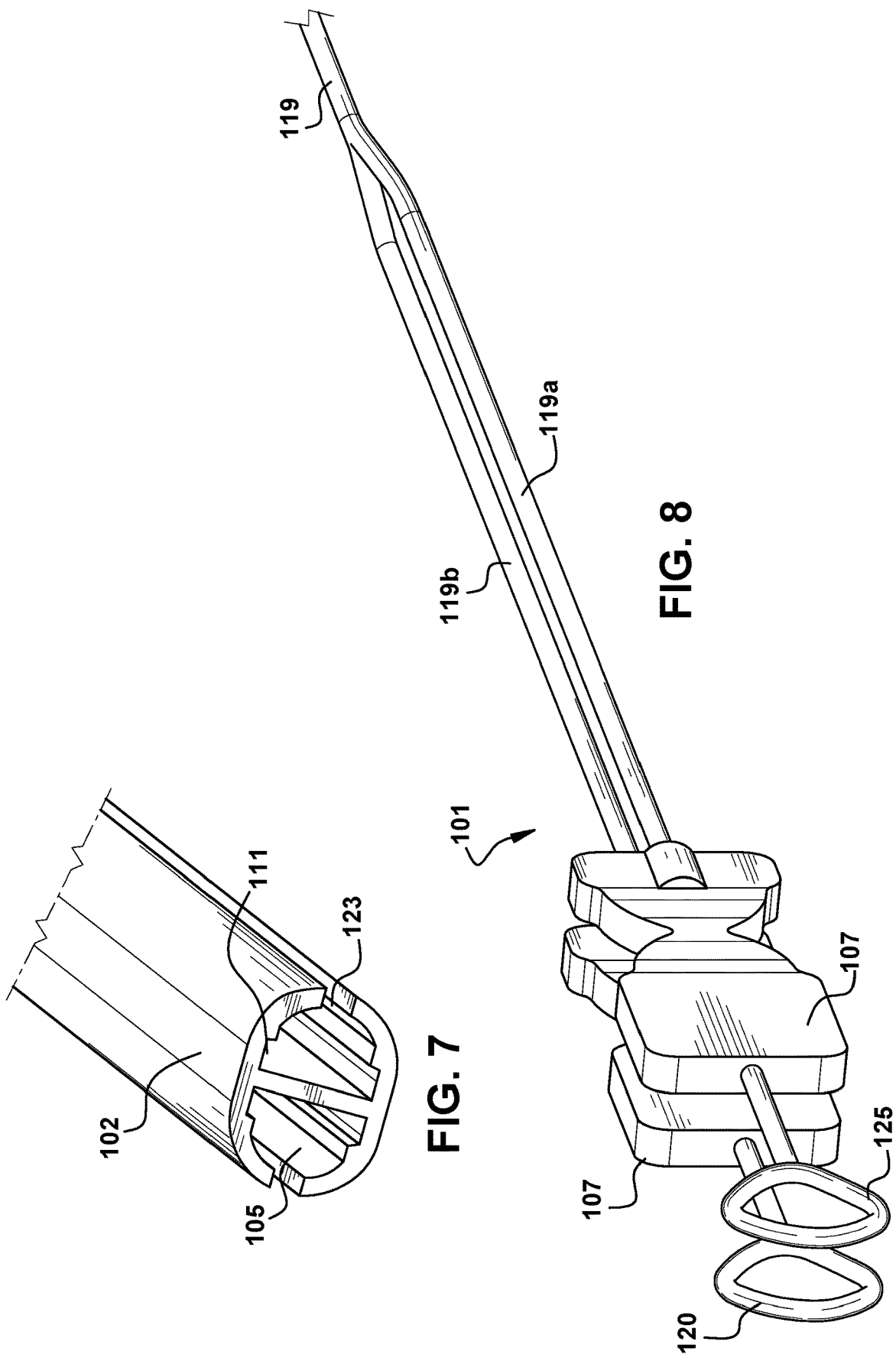

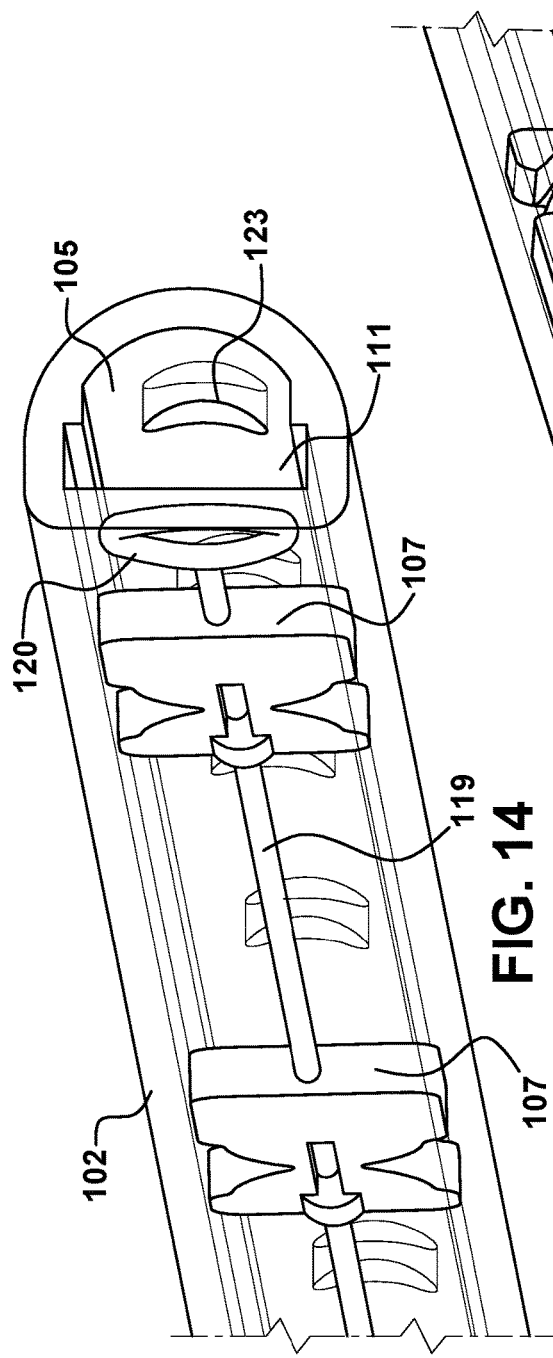
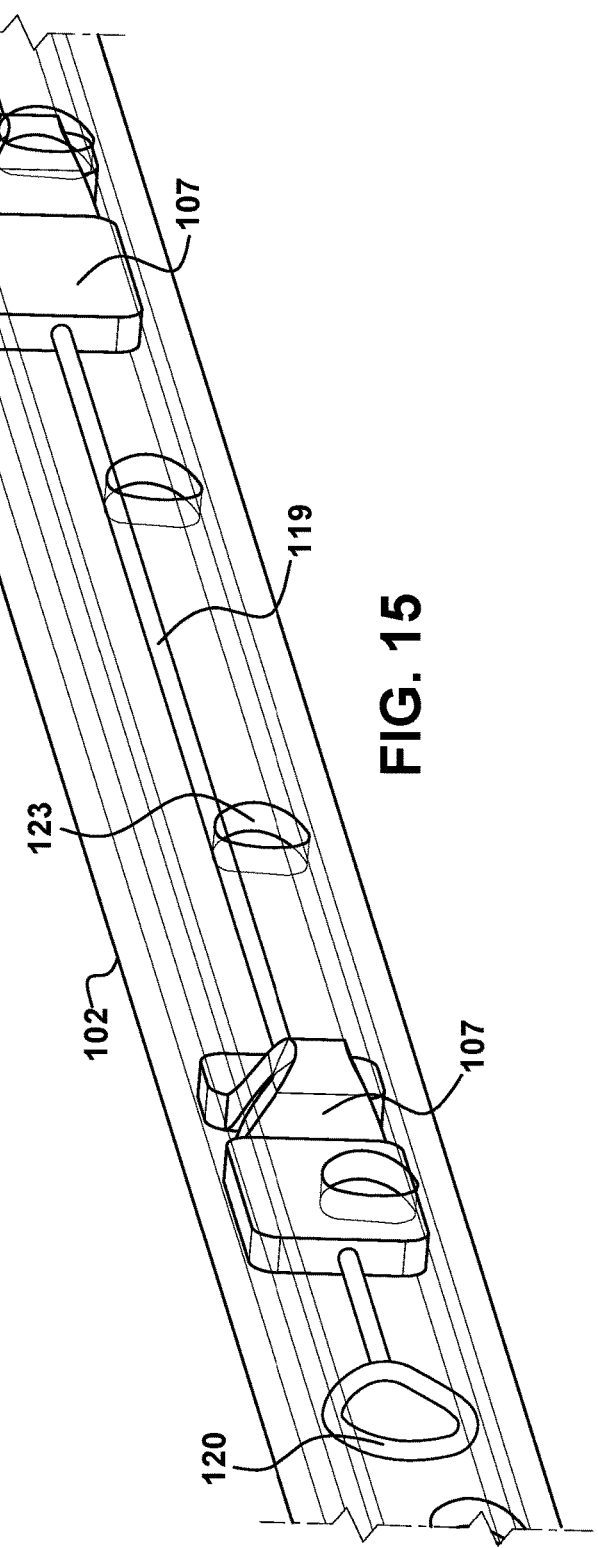
FIG. 14
FIG. 15

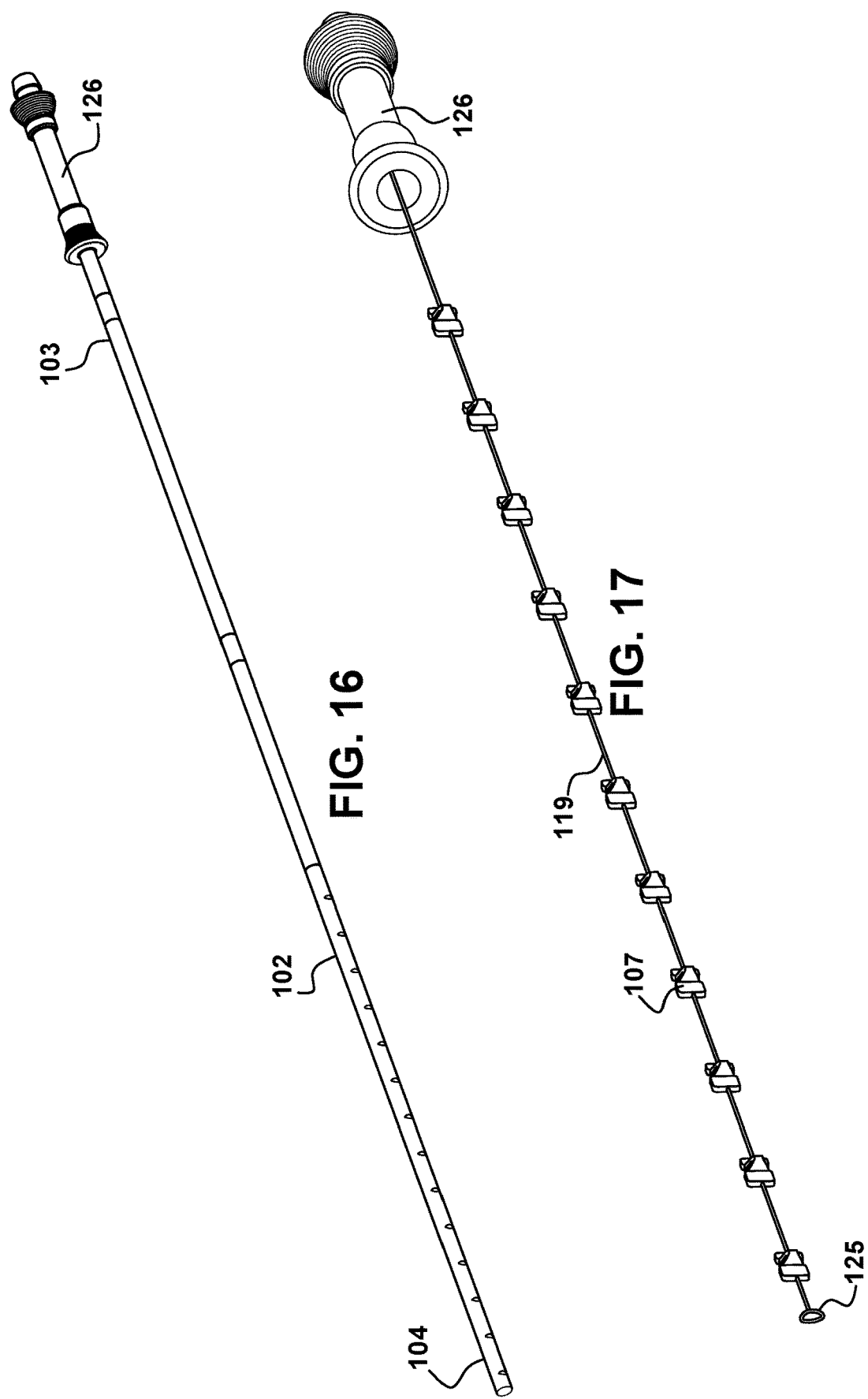

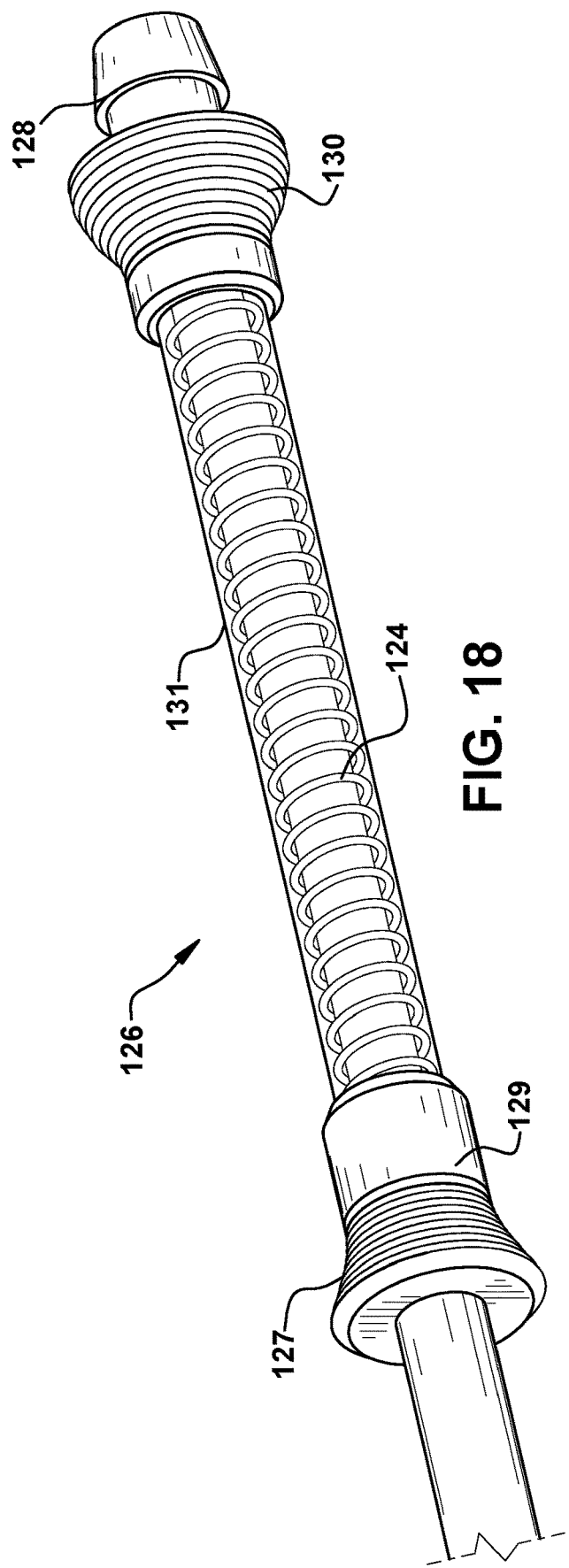

CLEARANCE SYSTEM FOR MEDICAL TUBES SUCH AS SURGICAL DRAINS

CROSS REFERENCE TO RELATED APPLICATIONS

This application claims priority to U.S. provisional patent application Ser. No. 62/941,252 filed Nov. 27, 2019, the contents of which are incorporated herein by reference.

TECHNICAL FIELD

This application relates generally to methods and devices to clear obstructive debris from medical tubes. More particularly, it relates to a device having a clearance member that resides in a medical tube and does not obstruct the free flow of material through the tube.

BACKGROUND

Medical tubes can be used to deliver fluids or devices into a body and/or to drain bodily fluids and secretions from compartments and structures within the body. For example, medical tubes can be used to drain fluid from one's bladder, from the colon or other portions of the alimentary tract, or from the lungs or other organs in conjunction with various therapies. Medical tubes also are used to drain blood and other fluids that typically accumulate within the body cavity following traumatic surgery. Typically, such a surgical drain tube is inserted into the patient so that its distal end is provided in or adjacent the space where it is desired to remove or deliver material while a proximal portion remains outside the patient's body, where it can be connected, for example, to a suction source.

Fluids passing through a medical tube (particularly those including blood or blood platelets) can form clots or other obstructions within the medical tube, which can partially or totally obstruct the suction pathway within the tube. Obstruction of the medical tube can impact its effectiveness to remove or deliver the fluid and other material for which it was originally placed, eventually rendering the medical tube partially or totally non-functional. In some cases, a non-functional tube can have serious or potentially life-threatening consequences. For example, if there is a blockage in a chest tube following cardiac or pulmonary surgery, the resulting accumulation of fluid around the heart and lungs without adequate drainage can cause serious adverse events such as pericardial tamponade and pneumothorax.

Methods and apparatus are desirable to keep medical tubes from clogging or to clear medical tubes reliably without having to breach the closed system between a suction source and the body cavity requiring drainage. Such methods and apparatus may allow for the placement of fewer tubes post-surgery, or to select tubes having smaller diameters, both of which will reduce patient discomfort and recovery time. Placement of fewer medical tubes also will minimize the risk of infection.

SUMMARY

A device for clearing obstructions from a medical tube is provided. The device includes an elongate guide member and a clearance member attached to the guide member. The clearance member is translatably received within a guide channel of a medical tube associated with a lumen thereof. The clearance member is configured such that advancement of the guide member will maintain the clearance member in a low-profile that does not impede flow through the lumen, and that withdrawal of the guide member causes the clearance member to assume an enlarged-profile within the lumen and effective to sweep the lumen upon withdrawal thereof.

A clearance member for clearing obstructions from a medical tube is also provided. The clearance member includes a first, low-profile conformation, and is axially compressible such it folds to thereby yield a second, enlarged conformation upon axial compression thereof.

BRIEF DESCRIPTION OF THE DRAWINGS

FIG. 1 is a perspective view of a clearance apparatus coupled to a medical tube;

FIG. 2 is a perspective view of a medical tube with openings (slits in the illustrated embodiment) in the sidewall of the tube extending along a portion of the length of the tube;

FIG. 2a is a close-up perspective view of a distal end of the medical tube of FIG. 2;

FIGS. 3 and 4 illustrate medical tubes having variable cross-sections along their respective lengths;

FIG. 3 is a side view of an exemplary partitioned medical tube as described herein;

FIG. 3a is a cross-sectional view of the medical tube of FIG. 3 taken along line A-A therein;

FIG. 3b is a cross-sectional view of the medical tube of FIG. 3 taken along line B-B therein;

FIG. 3c is a cross-sectional view of the medical tube of FIG. 3 taken along line C-C therein;

FIG. 4 is a side view of another exemplary partitioned medical tube as described herein;

FIG. 4a is a cross-sectional view of the medical tube of FIG. 4 taken along line A-A therein;

FIG. 4b is a cross-sectional view of the medical tube of FIG. 4 taken along line B-B therein;

FIG. 5 is a perspective view of a partitioned distal region of a medical tube with apertures in the sidewall thereof along a portion of its length;

FIG. 6 is a cross-sectional view of the partitioned region of the medical tube shown in FIG. 5 taken along line 6-6 therein with guide channels extending along lumens in the tube;

FIG. 7 is a perspective view of a partitioned distal region of a medical tube with openings (slits in the illustrated embodiment) in the sidewall of the tube extending along a portion of the length of the tube, and guide channels extending along lumens in the tube;

FIG. 8 is a perspective view of two clearance members in a first, low-profile configuration attached to or formed integrally with a guide member according to an embodiment hereafter described;

FIG. 14 is a perspective view of a distal end of a medical tube, with the tube shown in phantom and a plurality of clearance members attached to a guide member and positioned within a guide channel of a medical tube according to an embodiment hereafter described;

FIG. 15 is a further perspective view of the embodiment of FIG. 14;

FIG. 16 is a perspective view of a cleaning apparatus coupled to a medical tube according to an embodiment hereafter described;

FIG. 17 is a perspective view of the cleaning apparatus of FIG. 16 with the medical tube omitted;

FIG. 18 is a close-up perspective view of a handle assembly of the cleaning apparatus of FIG. 16;

DETAILED DESCRIPTION

Figure 10:
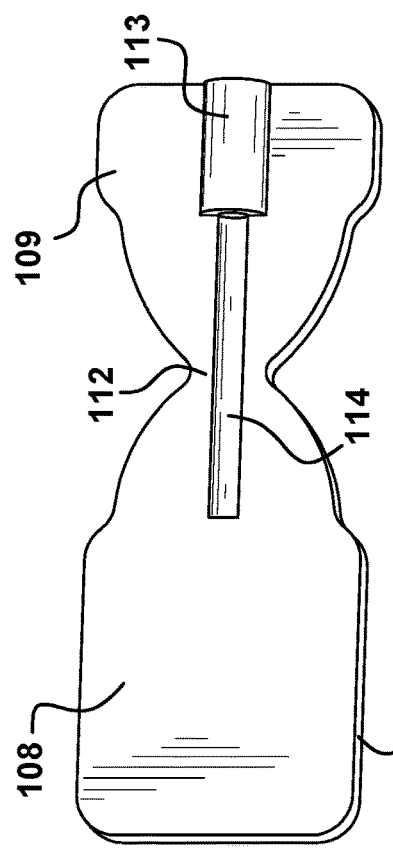
FIG. 10 is a side view of a second, opposing face of the clearance member in the low-profile configuration of FIG. 9.

As used herein, the terms proximal and distal are generally to be construed with reference to a patient that has been or is to be fitted with a medical tube, such as a chest tube. For example, the distal end or region of a medical tube (e.g. chest tube) is that end or region that is to be inserted into or disposed more adjacent (e.g. within) the patient during use, as compared to the opposite end or region of the medical tube (e.g. chest tube). Similarly, a distal element (or the distal side or region of an element) is nearer to the patient, or to the distal end of the chest tube, than a proximal element (or the proximal side or region of an element). Also herein, the "terminal" end of a tube, wire, or member refers to its distal end.

It is further to be noted that the term "coupled" as used herein when describing two or more features means that the features can be integral with each other or that the features can be separate features that are removably or non-removably attached to each other using various means such as threads, fasteners, hooks, clips, adhesive, welds, or other means of attaching two separate features. The features may be movably coupled to each other such that each feature is movable (e.g., slidable, rotatable, etc.) relative to the other, or the features may be fixedly coupled to each other such that neither feature can substantially move relative to the other.

Examples will now be described more fully hereinafter with reference to the accompanying drawings in which example embodiments are shown. Aspects may be embodied in many different forms and should not be construed as limited to the embodiments set forth herein.

Clearance apparatus as disclosed herein can be used with prior tubes having one or more lumens, wherein a guide channel 111 as herein described can be formed as part of or associated with one or more of those lumens, to accommodate a clearance device/apparatus as herein described. Such prior tubes are described in U.S. Publication No. 2015/0231361, herein incorporated by reference in its entirety. As will be appreciated, an intermediate portion of the clearance member can be designed so as to conform to the shape and dimensions of the cross-sectional area of a particular lumen in its enlarged conformation.

FIG. 1 shows a clearance apparatus 101 coupled to an exemplary medical tube 102 that is partitioned near its distal end 104. The medical tube 102 has at least one lumen and one or more openings 123 in fluid communication with one or more lumens within the tube 102. In the embodiment of FIG. 1, the medical tube includes only one lumen. The lumen extends from or near the distal end 104 to the proximal end 103 (indicated in FIG. 2). The openings 123 extend from at or near the distal end 104 along a portion of the length of the medical tube 102. In use fluid can be drawn into the lumen by capillary action or a pressure gradient (e.g. via a connected vacuum/suction source, vacuum pump, compressed bulb, or other means). FIGS. 2 and 2a more clearly illustrate the medical tube 102 with openings 123 along a portion of the length of the medical tube near its distal end 104. The medical tube 102 can be attached at its proximal end 103 to a clearance apparatus 101. Preferably, the medical tube 102 is made from a material having elastic properties, such as silicone, which will help ensure a fluid-tight seal. A flexible, elastic medical tube 102, e.g. made from silicone, also will result in reduced discomfort for the patient compared to more rigid medical-tube materials, such as polypropylene or polyethylene. However, if desired these and other rigid materials may be used. Other materials, including various thermoplastics and thermosets, also may be used in place of silicone, if desired. Preferably, the medical tube 102 is made from a clear (i.e. transparent or substantially transparent) plastic material, so the operator of the clearance apparatus 101 described herein can visualize any clot material or other debris therein, as well as its removal as described below. Aspects and embodiments of the medical tube 102 hereafter described can be applied directly or with minor and routine modifications to clear obstructive debris from a variety of medical tubes used in different applications, for example chest tubes, catheters, surgical drain tubes to drain fluid from other structures or orifices, endotracheal tubes, feeding tubes, gastric tubes, or tubes to deliver material to or from the alimentary tract, etc.

Exemplary embodiments of partitioned medical tubes will now be more fully described. As seen in FIGS. 3-4, medical tubes 102 can be provided that vary in cross-section along their lengths. In one embodiment illustrated in FIGS. 3-3c, a medical tube 102 having a generally round or circular perimeter (circumference) can include a plurality of regions having different cross-sections, each region having a respective number and arrangement of lumens or channels therein. The embodiment illustrated in FIGS. 3-3c includes three distinct regions: a proximal region whose cross-section is shown at FIG. 3a, an intermediate region whose cross-section is shown at FIG. 3b, and a distal region whose cross-section is shown at FIG. 3c.

The proximal region constitutes a single lumen such that this region is configured as a conventional tube. As shown in FIG. 3a, the medical tube 102 in this region is substantially hollow having a single lumen of open cylindrical cross-section. As shown in FIG. 3b the intermediate region is divided into four substantially equivalent wedge-shaped lumens arranged symmetrically as shown. As shown in FIG. 3c, in the distal region slits or apertures are disposed along the length of the tube 102 through its outer wall so that the wedge-shaped lumens in the intermediate region give way to correspondingly arranged and similarly-shaped channels that are open laterally to the space surrounding the tube 102 adjacent the exterior surface thereof, through the aforementioned slits or apertures. It is to be noted that as used herein, the term 'lumen' includes both enclosed passages, which are not open laterally to the outside of the medical tube, as well as channels, which are passages that are open to the outside via slits, apertures or other openings that provide fluid communication through the wall of the medical tube. A lumen also can be open to an adjacent lumen within the medical tube via slits, apertures or other openings, whether or not it is also open to the outside through the wall of the medical tube.

In another embodiment illustrated in FIGS. 4-4b, the medical tube 102 can be round in shape along a portion of its length near its proximal end 103 and transition into a flattened shape along a portion of its length near its distal end 104. This type of medical tube can be referred to as a flat channel drain. As shown in FIG. 4a taken along line A-A in FIG. 4, a first region of the medical tube 102 in this embodiment has a single lumen of open cylindrical cross-section similar to a conventional tube. But as one proceeds along its length toward the distal end, the medical tube 102 in this embodiment transitions from that of the first region described above adjacent the proximal end 103 to a second region adjacent the distal end 104, which has a flattened, oblong-shaped cross-section featuring two flat longer sides and two rounded shorter sides. FIG. 4b, taken along line B-B in FIG. 4, shows a cross-section of the medical tube 102 in this second region wherein the tube is partitioned into four distinct channels, two of which are substantially rectangular in cross-section and disposed opposite one another adjacent the opposed flat sides of the tube, and two of which are substantially semicircular in cross-section and disposed opposite one another adjacent the opposed curved sides. In the illustrated embodiment each of the channels is open to the environment immediately surrounding the tube via respective slits or apertures that provide fluid communication through the tube wall.

FIGS. 5 and 6 illustrate a partitioned medical tube 102 according to a further embodiment. Specifically, FIG. 5 shows the distal end of a medical tube 102, which is partitioned into four substantially equivalent quadrant lumens 105 arranged symmetrically as shown, each having an arcuate outer wall radially distant from the longitudinal axis of the tube 102, and a longitudinally-extending slot or guide channel 111 opposite the arcuate wall adjacent the axis. As better seen in FIG. 6, which shows a cross-section taken along line 6-6 in FIG. 5, the quadrant lumens 105 are separated and defined by substantially orthogonally, longitudinally-extending radial cross-members that substantially form a cross or plus sign (+) when viewed end-on. In this embodiment the guide channels 111 communicating with each of the respective lumens 105 are substantially circular in cross-section. As will be described below, in further embodiments the guide channels 111 can accommodate respective guide members (e.g. guide wires) for actuating, as by translation, associated clearance members also accommodated within the respective guide channels 111, and/or in the lumens 105.

FIG. 7 illustrates another partitioned medical tube 102 according to a further embodiment. Specifically, FIG. 7 shows the distal end of a medical tube 102, which is partitioned into two substantially equivalent lumens 105 arranged symmetrically as shown on either side of a central wall with each of the respective lumens 105 forming a substantially D-shaped cross-section. Each lumen 105 includes a longitudinally-extending guide channel 111 adjacent the central wall. In preferred embodiments the guide channels 111 can accommodate respective guide members (e.g. guide wires) for actuating, as by translation, associated clearance members also accommodated within the respective guide channels 111, and/or in the lumens 105.

FIG. 8 illustrates an embodiment of a clearance apparatus 101 for use with a medical tube 102; e.g. that shown in FIG. 7. The clearance apparatus 101 includes a guide member 119 (e.g. a guide wire) that can be advanced or withdrawn through the medical tube 102 to help dislodge or draw obstructing material within the medical tube 102. One or more clearance members 107 can be coupled to or adjacent a distal end 120 or other portions of the guide member 119 to aid in dislodging or drawing obstructing material as the guide member 119 translates through the medical tube 102. In the illustrated embodiment, the guide member 119 is circular in cross-section and is made of a material with elastic or shape-memory properties, such as, for example, stainless steel and nickel-titanium alloys. Further, the guide member 119 splits into first and second branches 119a and 119b in a distal region of the guide member. At or adjacent the distal end 120 of the guide member 119, each branch 119a and 119b includes a loop 125 that is sized and configured to be inserted and complementarily received within a respective guide channel 111 of the medical tube, thus guiding insertion and translation of the guide member 119 within the medical tube 102. However, the distal end 120 of the guide member 119 may include or be formed in other shapes that would be similarly complementarily received within the guide channels of the medical tube 102. Various examples of possible guide wires and clearance members are disclosed in U.S. Pat. No. 7,951,243 and U.S. patent application Pub. Nos. 2015/0231313 and 2015/0231361, which are incorporated by reference herein in their entirety.

Figure 9:
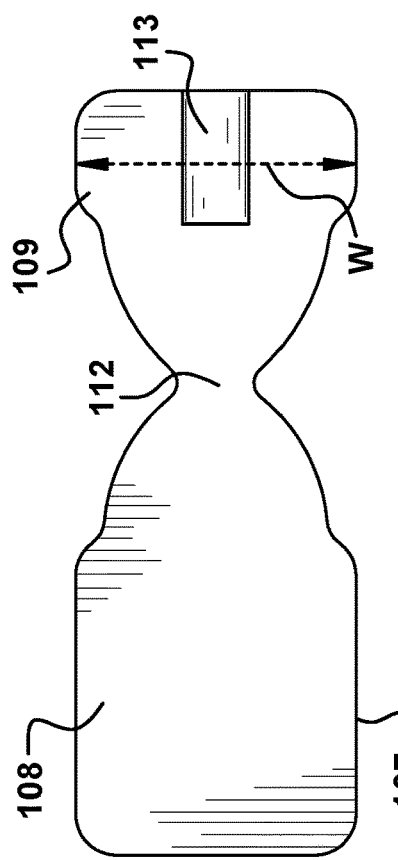
FIG. 9 is a side view of a first face of a clearance member in a first, low-profile configuration according to an embodiment hereafter described.

The clearance apparatus 101 illustrated in FIG. 8 also includes two clearance members 107 (one for each lumen 105 within the medical tube of FIG. 7), each in the form of a profile-expandable wiper coupled to each branch 119a and 119b of the guide member 119 near its distal end 120. Each clearance member 107, as shown in FIGS. 9 and 10, includes a distal portion 108, a proximal portion 109, and an intermediate foldable portion 112. In the illustrated embodiment, the foldable portion 112 features an hour-glass profile that when compressed axially will fold to create and conform to an enlarged profile that extends laterally from the channel 111 accommodating the proximal and distal portions 109 and 108 thereof, into the broader cross-section of the associated medical-tube lumen 105. As best seen in FIG. 15 (discussed below), the intermediate portion 112 is shaped so that in its enlarged profile it conforms substantially to a D-shape when viewed along a longitudinal axis of the medical tube (and the guide member 119), in order that it will conform to and preferably complement the D-shaped cross-section and dimensions of the associated lumen 105.

It is not critical that the intermediate portion 112 have an hourglass cross section. However, the intermediate portion 112 must have a reduced lateral dimension compared to each of the proximal and distal portions 109 and 108 of the clearance member 107 in order that on compression thereof, the intermediate portion 112 is free to assume its enlarged conformation, unconstrained by the channel 111. Conversely, the lateral dimensions of each of the proximal and distal portions 109 and 108 are large enough that upon axial compression of the clearance member 107 they remain constrained to slide along and within the channel 111 (e.g. coming closer together), and do not become unseated from within that channel 111 as the intermediate portion 112 expands to its enlarged conformation. The hourglass cross-section is preferred for the intermediate portion 112 because it facilitates folding of that portion at the location thereof where its lateral dimension is lowest. This enables one to determine with greater specificity where the intermediate portion 112 will fold upon compression, thus allowing design of the folded (enlarged) conformation cross-section based on the shape of the relatively wider sections of the hourglass shape in the intermediate portion 112.

The width W of the proximal region 109 preferably is such that it results in an interference fit within the opposing inner lateral surfaces of the guide channel 111 as the clearance member 107 translates therein.

The guide member 119 (or branch 119a, 119b thereof) passes through each of the proximal and distal regions of the clearance member 107 via a longitudinal receiving channel 114 that extends through both regions 108 and 109. The distal region 108 is fixed or securely attached to the guide member 119 (or branch 119a, 119b), e.g. via adhesive or an interference fit with that portion thereof passing through the part of the receiving channel 114 within the distal region 108. Whereas in the proximal region 109 the receiving channel 114 is dimensioned to permit translation of the guide member 119 (or branch 119a, 119b) therethrough, e.g. on drawing the guide member 119 proximally through the medical tube. For example, in at least the proximal region 109 the diameter of the receiving channel 114 can be slightly greater than the diameter of the guide member 119 (or branch 119a, 119b), which allows for the proximal region 109 to "float" on the guide member 119. In the intermediate region 112, the channel 114 is open and exposed along a face of the clearance member 117 opposite the greater cross-section of the lumen (i.e. opposite the lateral direction in which the intermediate member 112 will extend to achieve its enlarged profile). This enables the guide member to be fully accommodated within the channel 114 extending through the intermediate region 112 when in its low-profile, substantially flat conformation, while allowing the guide member to emerge from that channel in the intermediate region so as not to inhibit its assuming the enlarged profile upon actuation thereof (see FIG. 11).

Due to the friction from the interference fit between the proximal region 109 of the clearance member 107 (based its width W) and the lateral walls of the guide channel 111, proximal region 109 will tend to resist translation both in the proximal and distal directions. This resistance can be overcome by reasonable force, e.g. supplied by a caregiver or an actuation device in order to advance or withdraw the guide member 119 through the medical tube in use. In use, this means that upon advancement of the guide member 119 the entire clearance member 107 will be advanced through the guide channel 111 by virtue of its attachment to the distal region 108 thereof. Whereas, upon withdrawal of the guide member 119 the proximal region 109 provides resistance, such that the two regions 108, 109 will tend to be drawn together, wherein the intermediate portion 112 will be compressed axially and assume its enlarged conformation (again seen in FIG. 11). Because the proximal region 109 floats on the guide member 119, the guide member 119 is permitted to pass therethrough when retracted or withdrawn from the medical tube 102, such that the proximal region 109 can retain its position within the guide channel 111 due to friction therewith.

Figure 11:
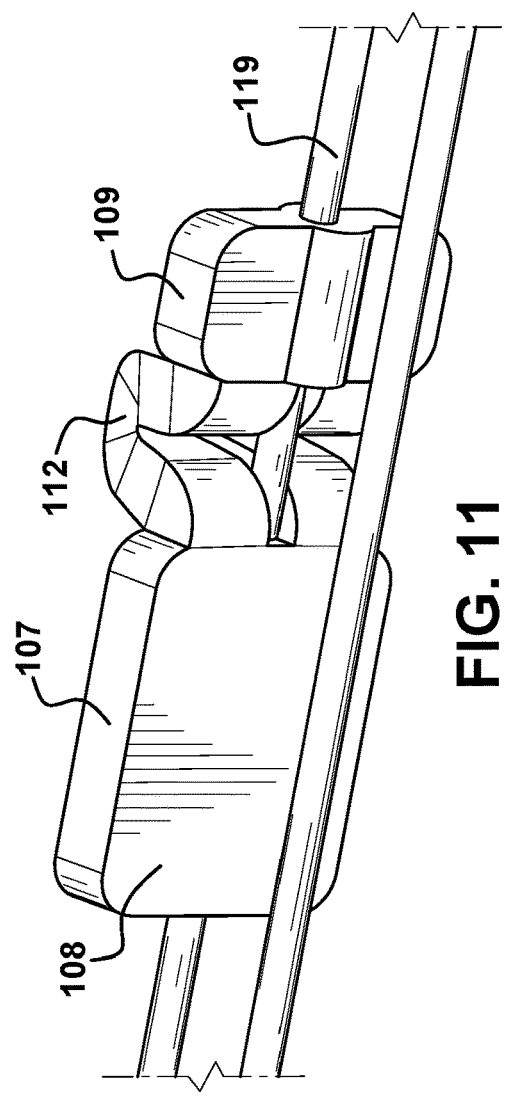
FIG. 11 is a perspective view of the clearance member of FIGS. 9 and 10 in a second, enlarged-profile configuration attached to or formed integrally with a guide member according to an embodiment hereafter described.

FIGS. 8 and 11 illustrate the clearance member 107 in a low-profile configuration and an enlarged-profile configuration, respectively. As shown in FIGS. 8 and 14, the clearance member 107 may normally reside within a medical tube 102 in a low-profile configuration. In this configuration, the guide member 119 and the clearance member 107 are positioned within the guide channel 111 of or associated with a lumen 105 of the medical tube 102. When in the low-profile configuration, the clearance member 107 does not significantly hinder or obstruct flow or drainage within the medical tube 102. That is, the clearance member 107 largely is removed from or not resident in the greater cross-section of the lumen 105. In order to remove obstructing material from that lumen within the medical tube 102, the guide member 119 is withdrawn from the medical tube 102. As the guide member 119 is withdrawn, the distal region 108 of the clearance member 107 moves towards the proximal end 103 of the medical tube 102. However, due to the friction between the proximal region 109 of the clearance member and the medical tube 102 as explained above, the proximal region 109 remains in place so that as the distal end 108 moves closer to the proximal end 103 the intermediate portion 112 of the clearance member 107 folds to yield a D-shaped wiper corresponding to the cross-sectional profile of the lumen 105 as seen in FIGS. 11 and Once in the enlarged-profile configuration, continued withdrawal of the guide member 119 will overcome the frictional resistance of the proximal region 109, thereby withdrawing the enlarged-profile clearance member 107 so that it engages and withdraws obstructing material within the lumen 105 in a proximal direction, toward and preferably out from the proximal end 103 thereof. Once the obstructing material has been removed from the lumen 105, the guide member 119 is advanced back to its original resting position. Because of the frictional resistance of the proximal region 109, such advancement will longitudinally expand the clearance member 107, which returns the clearance member 107 back to its original low-profile configuration.

The clearance member preferably is made from a material having elastic properties, such as a suitable elastomer or silicone. Other materials, including various thermoplastic and thermosets, also may be used in place of silicone, if desired.

Figure 12:
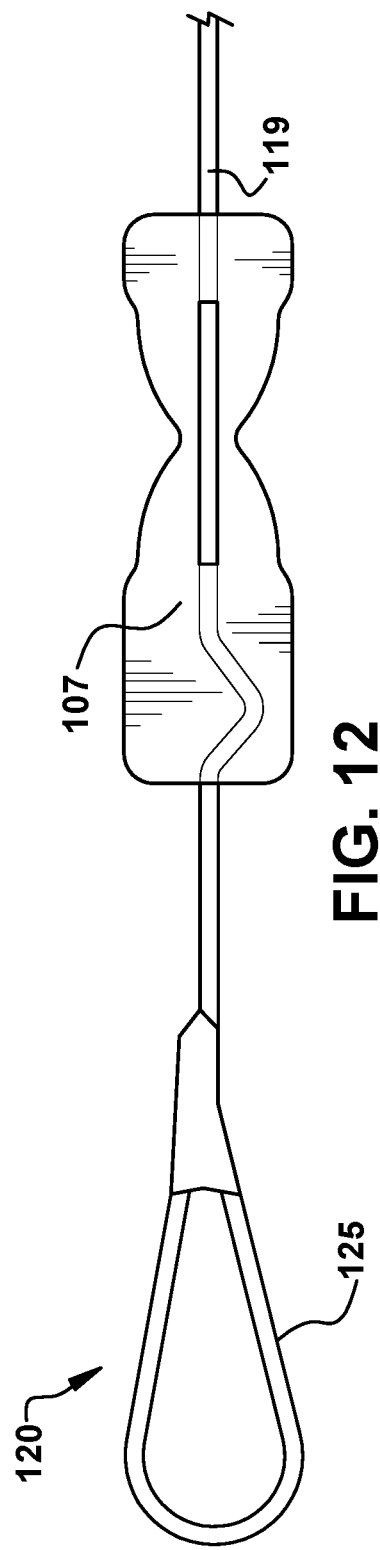
FIG. 12 is a side view of a clearance member according to another embodiment hereafter described.
Figure 13:
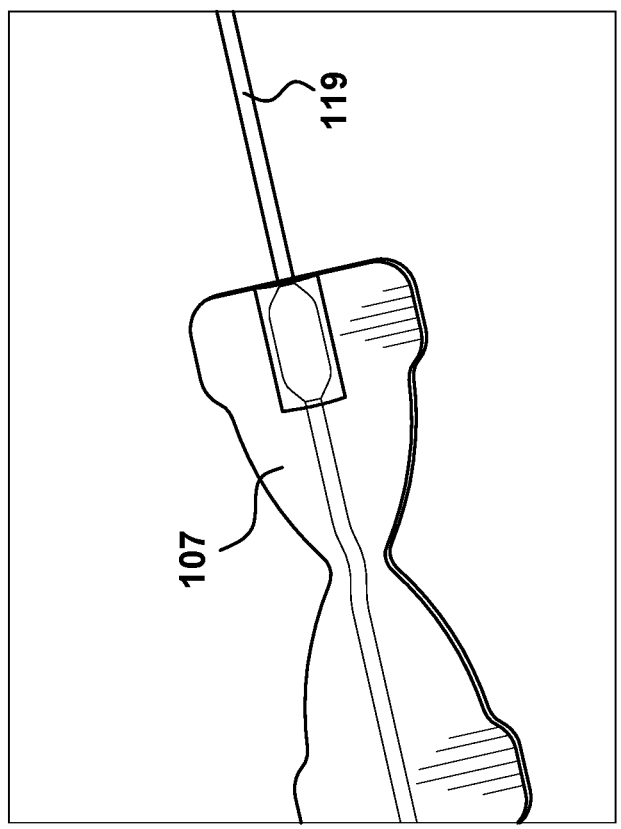
FIG. 13 is a close-up side view of the clearance member of FIG. 12.

FIGS. 12 and 13 illustrate an embodiment of a guide member 119 that includes a single wire and a single clearance member 107. The guide member 119 includes a loop 125 at its distal end 120 that has been formed integrally with and as part of the guide member 119. In this embodiment, the guide member 119 is formed having an elbow within the distal region of the clearance member 107, which facilitates affixation of the distal region thereto in a manner that will inhibit relative translation. The clearance member 107 then can be formed (e.g. molded and cured) over the guide member so that the receiving channel 114 follows a complementary elbow-shaped path through the distal region that will fixedly retain it to the guide member 119 upon translation. Meanwhile, the guide member 119 also is received in the portions of the receiving channel 114 that run linearly through the proximal region 109 and the intermediate portion 112 of the clearance member 107. In one embodiment as shown in FIG. 13, a bushing can be fitted over the portion of the guide member 119 passing through the proximal portion of the clearance member 107, which slidingly receives the guide member 119 therethrough. This bushing can be affixed within the proximal region of the clearance member 107 similarly as the guide member 119 is affixed within the distal region thereof; e.g. via direct over-molding of the clearance-member material over the bushing. Once molded therein, the bushing provides a relatively low-friction passage through which the guide member 119 can translate upon actuation thereof. In another embodiment, the bushing can be removed after molding, which results in the diameter of the receiving channel 114 being slightly greater than the diameter of the guide member 119, which allows for the proximal region 109 to "float" on the guide member 119.

The embodiments illustrated in FIGS. 8 and 11-13 show a single clearance member 107 positioned on a guide member 119 or a guide member branch 119a/119b. In additional embodiments illustrated in FIGS. 14-17, the clearance apparatus 101 includes a plurality of clearance members 107 positioned along the length of the guide member 119.

FIGS. 14 and 15 illustrate a guide member 119 having a plurality of clearance members 107 positioned thereon within a guide channel 111 of a lumen 105 of a medical tube 102. In this embodiment, the medical tube 102 features a single D-shaped lumen with openings 123 along an outer curved wall of the tube. FIG. 14 illustrates the clearance members 107 in a low-profile configuration, wherein draining of fluid through the lumen 105 would proceed in a substantially unobstructed manner. The distal end 120 of the guide member 119 resides in a resting position (i.e. "parked") at a distal end of the guide channel 111 within the medical tube 102. The guide member 119 is recessed within the distal end of the medical tube 102 when parked in order to prevent injury to a patient. In order to clear obstructing material with the lumen 105, the guide member 119 is retracted or withdrawn from within the medical tube 102, as shown in FIG. 15. As the guide member 119 is retracted or withdrawn, the intermediate portions 112 of the clearance members 107 fold and create D-shaped wipers with a profile that substantially matches the cross-section of the lumen 105 as discussed above. Moreover, because there are multiple such clearance members 107 along the length of the guide member 119, obstructive material can be simultaneously drawn toward the proximal end 103 of the medical tube 102 at different axial locations.

More specifically, the clearance apparatus 101 can be operated via successive, reciprocating actuation of the guide member 119, such that the guide member 119 is repeatedly withdrawn and advanced to clear obstructions. When operated in this manner, upon the first and each successive withdrawal motion of the guide member 119, each of the clearance members 107 attached along its length will be compressed axially to conform to its enlarged-profile within the lumen 105. Further withdrawal will cause the enlarged-profile intermediate portion 112 of each clearance member 107 to sweep the lumen 105 and draw proximally any obstructing material it encounters. At the completion of each withdrawal stroke, advancement of the guide member 119 will axially extend each clearance member 107, collapsing it to its low-profile conformation thus removing it from the greater cross-section of the lumen 105, leaving any proximally-swept obstructive material in-place as the clearance member 107 advances beyond it. At the conclusion of the advancement stroke, the guide member 119 once again is withdrawn in a second (and subsequent) withdrawal stroke, whereby obstructive material that was previously withdrawn to some degree in a prior withdrawal stroke now can be engaged and swept proximally by the next-proximal clearance member along the guide member 119. In this manner, cyclic reciprocating actuation of the guide member 119 can be effective to withdraw obstructive material along substantially the full length of the lumen 105 that is swept by clearance members 107, in a stepwise fashion until all such material leaves the proximal end of the lumen 105.

FIGS. 16-18 illustrate embodiments of a handle assembly 126 for actuating the guide member 119, and correspondingly a plurality of clearance members 107 attached periodically along its length, to clear obstructive debris in medical tubes 102. Referring first to FIG. 16, the handle assembly 126 is effective to translate the guide member 119, and therefore the clearance members 107, within a lumen 105 of a medical tube 102, e.g. a chest tube. The medical tube 102 can be coupled to the handle assembly 126 via a medical-tube fitting 127 (see FIG. 18), which preferably has an internal diameter that is in continuity with the medical tube 102 at least at the point of attachment. The handle assembly 126 can also be connected to a vacuum drainage tube or other suction source (not shown) through a suction fitting 128 disposed at the proximal end of the handle assembly 126. The handle assembly 126 defines therein a conduit or passageway between the proximal and distal ends (i.e. between medical-tube and suction fittings 127 and 128), so that debris evacuated from the medical tube 102 can be drawn through the handle assembly 126 via a suction source. A guide member 119, e.g. according to any of the embodiments above described, is secured to or within the handle assembly 126 at or adjacent the guide member's 119 proximal end.

FIG. 17 illustrates the actuation device wherein the medical tube 102 has been omitted in order to more clearly show the guide member 119 and plurality of spaced-apart clearance members 107 attached thereon.

FIG. 18 illustrates an exemplary embodiment of a handle assembly 126 of a clearance apparatus 101 having or defining an adjustable-length guide tube 131, in which the guide tube 131 is made of a flexible material that is elastically stretchable, such as a suitable elastomer or silicone. The adjustable-length guide tube 131 surrounds and is supported by a coil spring 124 that both defines its length and lends structural support to reinforce its diameter, and thereby that of the passage therein through which obstructive material may be drawn via suction or other means. The coil spring can be made of any suitable material such as from metal or polymer wires or strands, having a modulus of elasticity.

The handle assembly 126 includes distal and proximal handle portions 129 and 130 that are longitudinally separable from one another. The adjustable-length guide tube 131 is connected at opposite ends thereof to, and extends between, handle portions 129 and 130 in order to define a substantially cylindrical and variable-length passageway therein. This passageway in use will cooperate to partially define a closed suction pathway (preferably preserving a sterile field therein) between a medical tube 102 and a suction source. As will be appreciated from FIGS. 16 and 18, as the handle portions 129 and 130 are separated, the tube 131 will extend, thus lengthening the guide tube 131. Conversely, as the handle portions 129 and 130 are brought together (and optionally brought into contact with one another), the guide tube 131 is collapsed thus lowering its effective length. In preferred embodiments, the coil spring is a compression spring whose resting conformation corresponds to the fully (axially) collapsed conformation of the guide tube 131, which in-use will correspond to a fully inserted condition of the guide member 119 (within the medical-tube lumen 105), whose proximal end is attached or affixed relative to the proximal handle portion 130. In other words, the collapsed conformation of the adjustable-length guide tube 131 corresponds to the full-inserted, resting position of the guide member 119, and therefore of the clearance member(s) 107 attached thereto within a medical tube 102.

The guide member 119 passes through the handle assembly 126, and is secured at its proximal end to the proximal handle portion 130 as noted above. In this manner, as the length of the adjustable guide tube 131 is increased by separating handle portions 129 and 130, the clearance member(s) 107 attached to the guide member 119 can be withdrawn from within a medical tube 102 as above described. Conversely, collapsing the guide tube 131 will advance the guide member 119 attached to the handle assembly 126 through the medical tube 102, e.g. to restore it to a resting or parked position adjacent the medical-tube distal end 104.

In order to clear obstructing material from the medical tube 102, a user would grasp the distal handle portion 129 and simultaneously grasp the proximal handle portion 130, and draw the proximal handle portion 130 away from the distal handle portion 129. As the effective length of the tubing in the handle assembly 126 is increased when stretched, a normally in-dwelling guide member 119, and associated clearance member(s) 107 (i.e. that normally rest (s) within the medical tube 102) will be drawn proximally through the medical tube. Separation of the handle portions 129 and 130 is resisted by the elastic modulus of the adjustable-length guide tube 131 itself. As the clearance member(s) 107 is(are) withdrawn from the medical tube 102, the intermediate foldable portion 112 of each clearance member 107 folds to yield the D-shaped wiper. The clearance member 107 can thus clear debris in the lumen(s) served by the clearance member 107 by drawing obstructive debris proximally, toward the handle assembly 126. While continuing to hold the distal handle portion 129 with one hand, the user can return the proximal handle portion 130 back to its original location and the elastic portion of the handle assembly 126 will shrink back to its original length, advancing the guide member 119 and clearance member(s) 107 back to its(their) original resting position. During this operation, care should be taken not to stretch the handle assembly 126 (or its elastic portion) so far that the clearance member 107 becomes completely withdrawn from the medical tube 102. If the clearance member 107 is completely withdrawn from the medical tube 102, a user would reinsert the guide member 119 and associated clearance member(s) 107 into the guide channel 111 of each lumen 105 of the medical tube 102. The user can repeat these steps to translate the clearance member 107 through the medical tube 102, or a portion thereof, as described in detail above in order to dislodge blood, clots, and other debris that may have accumulated along the length of the lumen(s) within the medical tube. Loosened blood, clots, and other debris then can drain from the lumen of the medical tube 102 through the fitting 127 into the handle assembly 126, and then through the fitting 128 to the vacuum drainage tubing and into a drainage receptacle (not shown). Suction is generally applied to the drainage receptacle to facilitate the drainage along this pathway.

Figure 19:
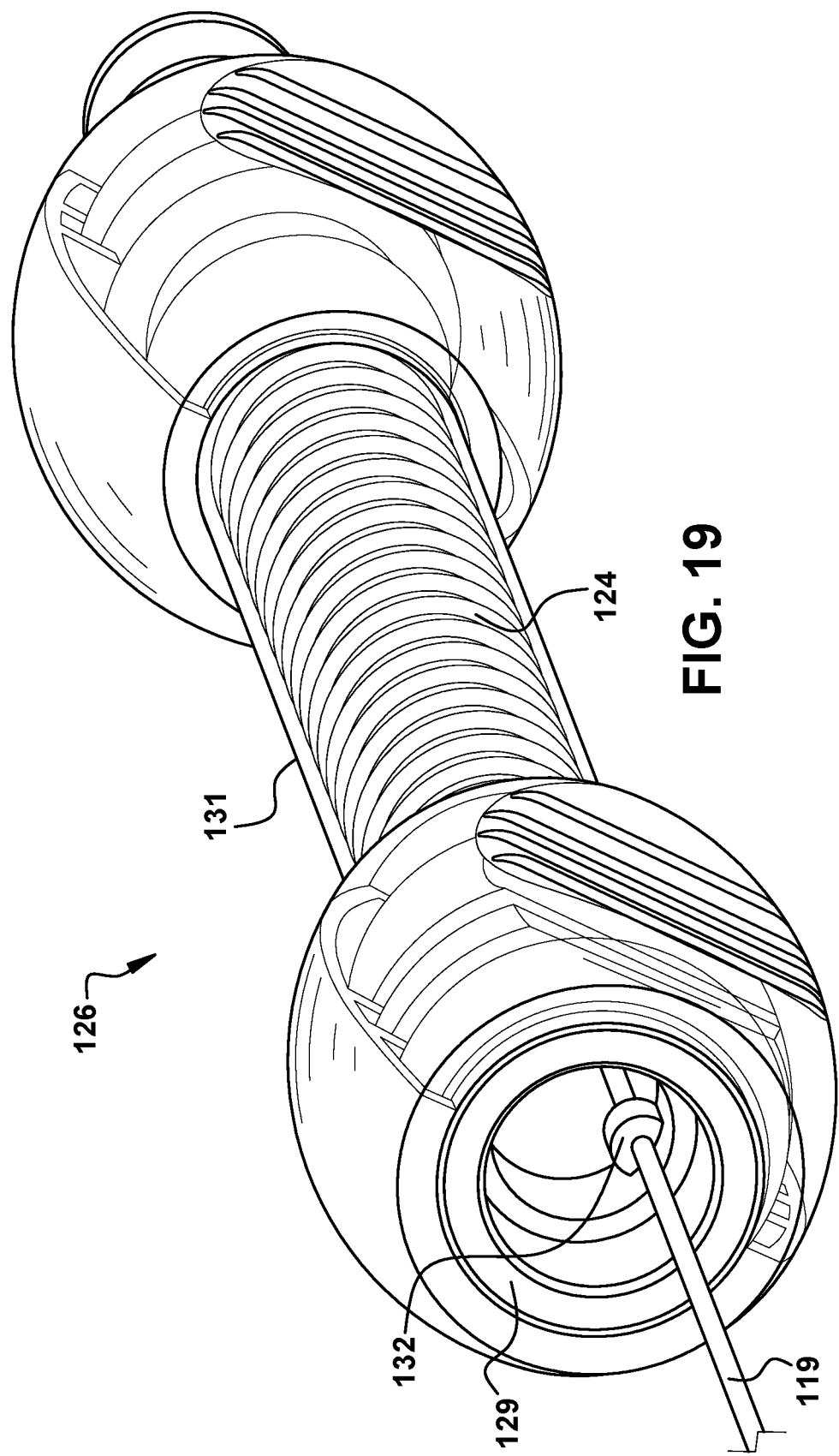
FIGS. 19-21 are perspective views of a handle assembly with a guide member stop that prevents the clearance member from being completely withdrawn from the medical tube according to an embodiment hereafter described.
Figure 20:
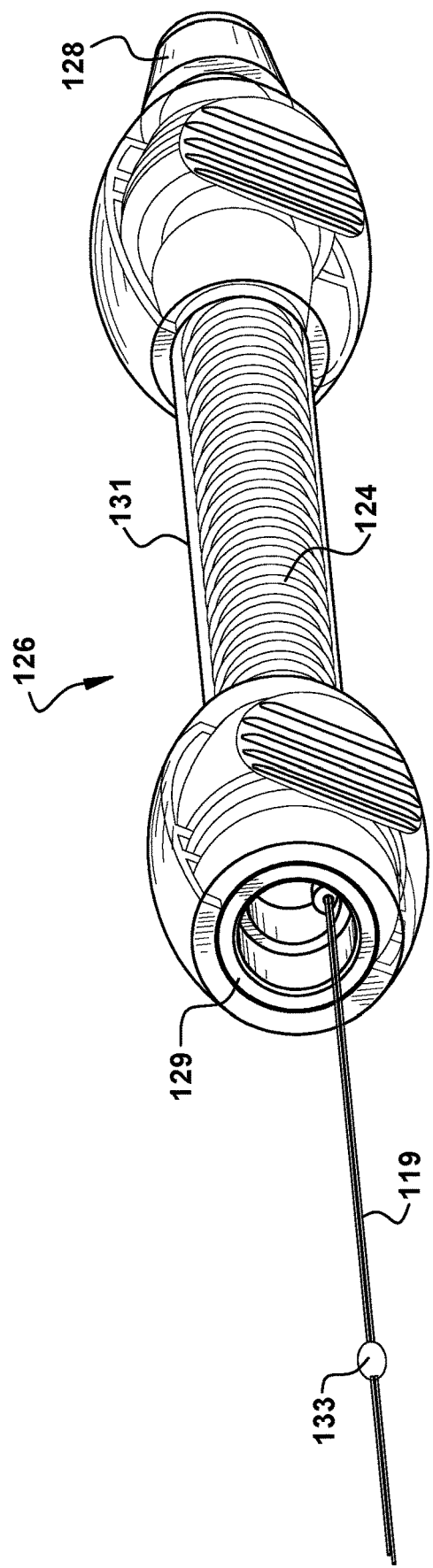
Figure 21:
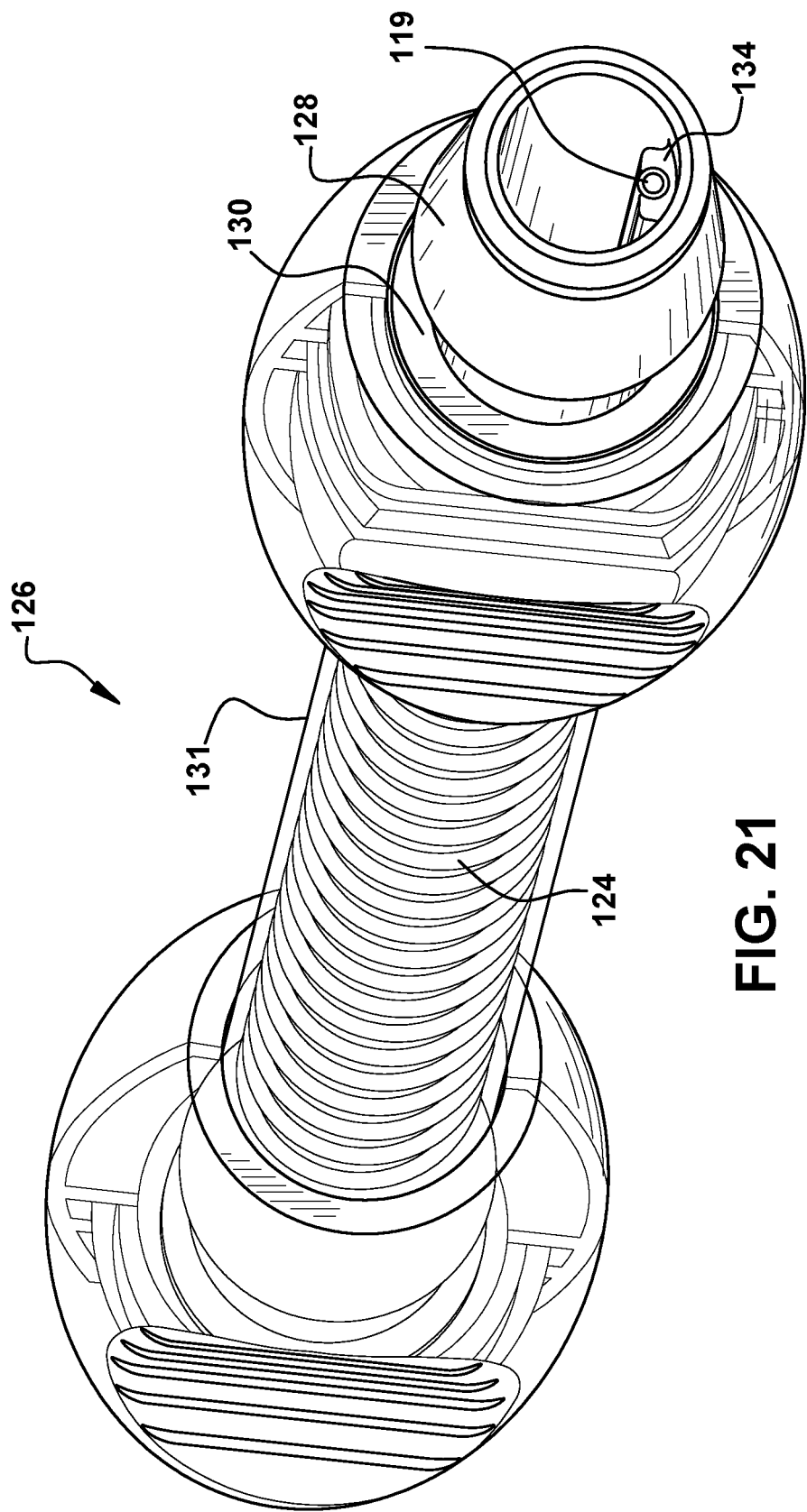

In a further embodiment illustrated in FIGS. 19-21, a guide member stop 132 is secured to an interior wall of the distal handle portion 129 of the handle 126. In the illustrated embodiment, the guide member stop 132 has a receiving channel, the diameter of which can be slightly greater than the diameter of the guide member 119. A stop element 133 is secured to the guide member 119 in a proximal region thereof. The stop element 133 is shown as a bead that has been crimped on the guide member 119. However, the stop element 133 can also be a portion of the guide member 119 that has a greater diameter than the diameter of the receiving channel of the guide member stop 132; e.g. a spiral-wound portion thereof. As shown in FIG. 21, the proximal handle portion 130 of the handle 126 includes a receiving channel 134 for a proximal portion of the guide member 119. As the guide member 119 is withdrawn (i.e. as the proximal handle portion 130 is drawn away from the distal handle portion 129), the stop element 133 approaches and ultimately reaches the guide member stop 132 wherein the respective stop element 133 is in contact or disposed adjacent to the guide member stop 132. In this manner, the guide member 119 is prevented from being withdrawn further from the medical tube lumen. The stop element 133 can be made from similar or the same material as the guide member 119 discussed above.

Figure 22:
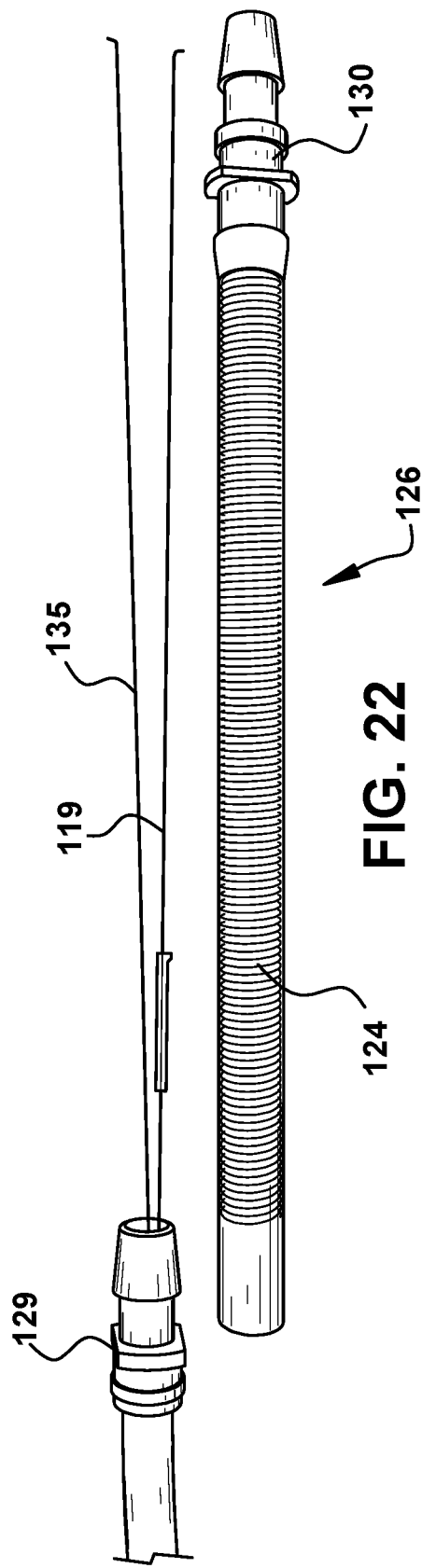
FIGS. 22 and 23 are perspective views of a handle assembly with a stop wire that prevents the clearance member from being completely withdrawn from the medical tube according to an embodiment hereafter described.
Figure 23:
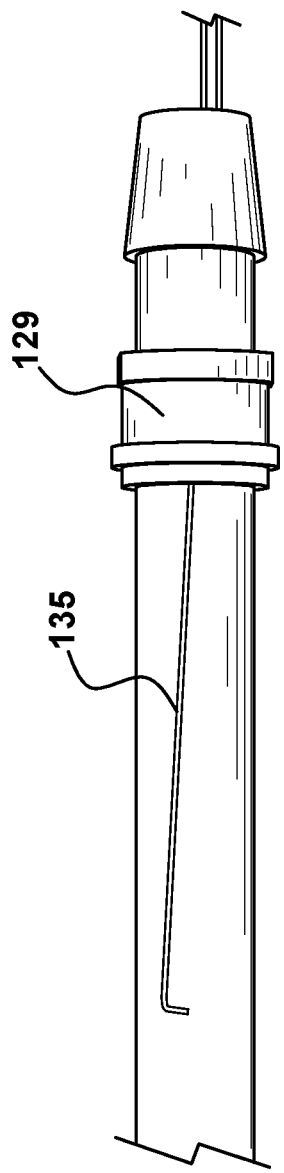

In a further embodiment illustrated in FIGS. 22 and 23, the handle assembly 126 includes a separate stop wire 135 that prevents the proximal and distal handle portions 130 and 129, respectively, from being pulled apart more than a predetermined distance as an alternative means of preventing the guide member 119 from being withdrawn from the medical tube lumen. In this embodiment, the distal handle portion 129 again includes the guide member stop 132 secured to an interior wall thereof. The guide member stop 132 has a receiving channel 135 as noted above, the diameter of which is such that the stop wire 135 and the guide member 119 can be simultaneously disposed within and pass through the guide member stop 132. The guide member 119 and the stop wire 135 pass through the handle assembly 126, and are secured at their proximal ends to the proximal handle portion 130 as noted above. As shown in FIG. 23, the stop wire 135 extends past the distal handle portion 129, but does not extend to the distal end of the medical tube, such that the stop wire 135 is shorter in length than the guide member 119. Further, the stop wire 135 is bent or crimped at or adjacent its distal end. In another embodiment, the stop wire 135 includes a stop element disposed at or adjacent its distal end. As the guide member 119 and the stop wire 135 are withdrawn (i.e. as the proximal handle portion 130 of the handle 126 is drawn away from the distal handle portion 129), the bend or crimp at or adjacent the distal end of the stop wire 135 approaches and ultimately reaches the guide member stop 132 wherein the bend or crimp is in contact or disposed adjacent to the guide member stop 132. In this manner, the guide member 119 is prevented from being withdrawn further from the medical tube lumen, as the proximal handle portion 130 can no longer be drawn away from the distal handle portion 129 without excessive force. The stop wire 135 can be made from similar or the same material as the guide member 119 discussed above.

In another embodiment, the length of the guide member 119 may be calibrated to ensure that the (distal-most) clearance member 107 is not advanced beyond the distal end 104 of the medical tube 102 in use. For example, the length of the guide member 119 and the position of its (distal most) clearance member 107 together preferably substantially approximate the distance from the guide member's point of attachment with the handle assembly 126 to just short of the distal end 104 of the medical tube 102.

Illustrative embodiments have been described, hereinabove. It will be apparent to those skilled in the art that various modifications and variations can be made without departing from the spirit and scope of the claimed invention. It is intended to include all such modifications and alterations within the scope of the present invention.

What is claimed is:

1. A device for clearing obstructions from a medical tube, comprising an elongate guide member and a clearance member attached to the guide member, the clearance member being translatably received within a guide channel of the medical tube adjacent to a drainage lumen of the medical tube, said clearance member being configured such that advancement of said guide member will maintain said clearance member in a low-profile that does not impede flow through said drainage lumen, and that withdrawal of said guide member causes said clearance member to assume an enlarged-profile within said drainage lumen and sweep the drainage lumen upon withdrawal thereof, said clearance member being disposed entirely within said guide channel while advancing said guide member.

2. The device of claim 1, the clearance member comprising a distal region, a proximal region and an intermediate region, wherein the intermediate region has a lower lateral width than each of said proximal and distal region.

3. The device of claim 1, wherein a plurality of clearance members are positioned along a length of the guide member.

4. The device of claim 2, the intermediate region of said clearance member being configured to complement a shape and dimensions of a cross-sectional area of said drainage lumen in the medical tube when in said enlarged-profile configuration.

5. The device of claim 1, the guide member being a guide wire, the clearance member being disposed at a distal end of the guide member.

6. The device of claim 1, further comprising an adjustable-length handle assembly connected in fluid communication with the medical tube and cooperating therewith to at least partially define a pathway through which obstructions can be evacuated from the medical tube.

7. The device of claim 6, the elongate guide member extending through the adjustable-length handle assembly and the medical tube, wherein extension of the adjustable-length handle assembly results in withdrawal of the guide member relative to the medical tube and collapse of the adjustable-length handle assembly results in advancement of the guide member relative to the medical tube.

8. The device of claim 1, the clearance member having a distal region, a proximal region and an intermediate region therebetween, said clearance member being axially compressible such that the clearance member folds to thereby yield the enlarged profile upon axial compression thereof, wherein upon said axial compression said proximal and distal regions are brought closer together thereby causing said intermediate region to fold and conform substantially to a D-shape when viewed along a longitudinal axis of the clearance member.

9. The device of claim 8, said intermediate region having an hourglass shape.

10. The device of claim 8, the clearance member being substantially flat in said low-profile.

11. The device of claim 1, wherein an interference fit is maintained between the clearance member and an inner surface of the guide channel during said advancement and said withdrawal of said guide member.

12. The device of claim 1, wherein said guide channel and said drainage lumen have different respective shapes in cross-section.

* * * * *